US011603350B2

(12) United States Patent
Fukushima et al.

(10) Patent No.: US 11,603,350 B2
(45) Date of Patent: Mar. 14, 2023

(54) COMPOUND, COMPOSITION, CURED OBJECT, OPTICALLY ANISOTROPIC BODY, AND REFLECTIVE FILM

(71) Applicant: FUJIFILM Corporation, Tokyo (JP)

(72) Inventors: Yuki Fukushima, Kanagawa (JP); Ryoji Goto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1065 days.

(21) Appl. No.: 16/275,324

(22) Filed: Feb. 14, 2019

(65) Prior Publication Data

US 2019/0177268 A1 Jun. 13, 2019

Related U.S. Application Data

(63) Continuation of application No. PCT/JP2017/028996, filed on Aug. 9, 2017.

(30) Foreign Application Priority Data

Aug. 17, 2016 (JP) .............................. JP2016-160179

(51) Int. Cl.

| | | |
|---|---|---|
| *C07C 235/56* | (2006.01) | |
| *C07C 69/92* | (2006.01) | |
| *C07D 277/74* | (2006.01) | |
| *G02B 1/04* | (2006.01) | |
| *C08F 38/02* | (2006.01) | |
| *C07C 323/62* | (2006.01) | |
| *G02B 5/08* | (2006.01) | |
| *C08F 22/26* | (2006.01) | |
| *C09K 19/18* | (2006.01) | |
| *C09K 19/22* | (2006.01) | |
| *C09K 19/34* | (2006.01) | |
| *C09K 19/04* | (2006.01) | |
| *G02B 5/30* | (2006.01) | |

(52) U.S. Cl.
CPC ............ *C07C 235/56* (2013.01); *C07C 69/92* (2013.01); *C07C 323/62* (2013.01); *C07D 277/74* (2013.01); *C08F 22/26* (2013.01); *C08F 38/02* (2013.01); *C09K 19/18* (2013.01); *C09K 19/22* (2013.01); *C09K 19/3497* (2013.01); *G02B 1/04* (2013.01); *G02B 5/08* (2013.01); *C09K 2019/0448* (2013.01); *C09K 2019/181* (2013.01); *G02B 5/3016* (2013.01)

(58) Field of Classification Search
CPC .... C09K 19/18; C09K 19/22; C09K 19/3497; C09K 2019/0444; C09K 2019/0448; C09K 2019/181; C08F 38/02; C07C 235/56
See application file for complete search history.

(56) References Cited

U.S. PATENT DOCUMENTS

| | | |
|---|---|---|
| 6,514,578 B1 | 2/2003 | Farrand |
| 2002/0048639 A1 | 4/2002 | Negoro et al. |
| 2017/0183286 A1 | 6/2017 | Androsov et al. |
| 2019/0177268 A1* | 6/2019 | Fukushima ............. C08F 22/26 |

FOREIGN PATENT DOCUMENTS

| | | | |
|---|---|---|---|
| EP | 1079244 | 2/2001 | |
| JP | 2002098836 | 4/2002 | |
| JP | 2003262728 | 9/2003 | |
| JP | 2013014538 | 1/2013 | |
| WO | WO2018/042924 A1 * | 3/2018 | ............... G02B 5/20 |

OTHER PUBLICATIONS

"International Search Report (Form PCT/ISA/210) of PCT/JP2017/028996," dated Sep. 19, 2017, with English translation thereof, pp. 1-5.
"International Preliminary Report on Patentability (Form PCT/IPEA/409) of PCT/JP2017/028996," completed on Nov. 20, 2018, with English translation thereof, pp. 1-9.
Annick Vidonne et al., "Integrating replication processes with mechanically interlocked molecular architectures," Tetrahedron, vol. 64, Issue 36, Sep. 1, 2008, pp. 8464-8475.
Annick Vidonne et al., "Exploiting recognition-mediated assembly and reactivity in [2]rotaxane formation," Chemical Science, vol. 7, Issue 4, Jan. 15, 2016, pp. 2592-2603.

* cited by examiner

*Primary Examiner* — Geraldina Visconti
(74) *Attorney, Agent, or Firm* — JCIPRNET

(57) ABSTRACT

The present invention provides a compound, a composition, a cured object, an optically anisotropic body, and a reflective film which have high refractive index anisotropy Δn and excellent light resistance, and which exhibit liquid crystallinity. The compound of the present invention is a compound represented by General Formula (1).

$$P^1-L^1-(A^1-Z^1)_{m1}-A^2=\!=\!=\!-A^3-Y-A^4-(Z^2-A^5)_{m2}-L^2-P^2$$

General Formula (1)

20 Claims, No Drawings

COMPOUND, COMPOSITION, CURED OBJECT, OPTICALLY ANISOTROPIC BODY, AND REFLECTIVE FILM

CROSS-REFERENCE TO RELATED APPLICATIONS

This application is a Continuation of PCT International Application No. PCT/JP2017/028996 filed on Aug. 9, 2017, which claims priority under 35 U.S.C. § 119(a) to Japanese Patent Application No. 2016-160179 filed on Aug. 17, 2016. The above application is hereby expressly incorporated by reference, in its entirety, into the present application.

BACKGROUND OF THE INVENTION

1. Field of the Invention

The present invention relates to a compound, a composition, a cured object, an optically anisotropic body, and a reflective film.

2. Description of the Related Art

A compound (hereinafter also simply referred to as liquid crystal compound) that exhibits liquid crystallinity can be applied to various uses. For example, the liquid crystal compound is applied to production of an optically anisotropic body typified by a retardation film, or to production of a reflective film for immobilizing a cholesteric liquid crystalline phase.

As the liquid crystal compound, for example, the tolan compound having a tolan skeleton (diphenylacetylene skeleton) described in U.S. Pat. No. 6,514,578B is mentioned. In such a tolan compound, an ester group is linked to the tolan skeleton.

SUMMARY OF THE INVENTION

On the other hand, for the liquid crystal compound, there is a demand for improvement in various properties.

For example, there is a demand for improvement in refractive index anisotropy Δn (hereinafter also simply referred to as Δn) of the liquid crystal compound. In a cholesteric liquid crystalline phase formed using such a liquid crystal compound with high Δn, a widened reflection band is exhibited, and an improved reflection efficiency is also exhibited.

In addition, from the viewpoint of handling properties, there is also a demand for improvement in light resistance of the liquid crystal compound.

In view of the above circumstances, an object of the present invention is to provide a compound which has high refractive index anisotropy Δn and excellent light resistance and which exhibits liquid crystallinity.

In addition, another object of the present invention is to provide a composition, a cured object, an optically anisotropic body, and a reflective film which contains the compound.

As a result of intensive studies on the above-mentioned objects, the present inventors have found that desired effects can be obtained by introducing an amide group at a predetermined position in a compound having a tolan skeleton.

That is, the present inventors have discovered that the above-mentioned objects can be achieved by the following constitution.

(1) A compound represented by General Formula (1) as described later.

(2) The compound according to (1),
in which at least one of $A^2$, . . . , or $A^4$ is an aromatic hydrocarbon ring group having a substituent, or an aromatic heterocyclic group having a substituent.

(3) The compound according to (2),
in which the substituent is a fluorine atom, a chlorine atom, a fluoroalkyl group, an alkoxy group, or an alkyl group.

(4) The compound according to (2) or (3),
in which the substituent is a fluoroalkyl group, an alkoxy group, or an alkyl group.

(5) The compound according to any one of (1) to (4),
in which $Z^1$ and $Z^2$ are each independently a single bond, —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, or —C≡C—.

(6) The compound according to any one of (1) to (5),
in which $Z^1$ and $Z^2$ are each independently a single bond, —COO—, —OCO—, —CO—NH—, —NH—CO—, or —C≡C—.

(7) The compound according to any one of (1) to (6),
in which $L^1$ is a group represented by General Formula (2) as described later, and $L^2$ is a group represented by General Formula (3) as described later.

(8) The compound according to (7),
in which $X^1$ and $X^2$ are each independently a single bond, —O—, —OCO—, or —OCO—.

(9) The compound according to (7) or (8),
in which n1 and n2 are each 1.

(10) The compound according to any one of (1) to (9),
in which m1+m2 is 0 or 1.

(11) A composition comprising:
the compound according to any one of (1) to (10).

(12) The composition according to (11), further comprising a polymerization initiator.

(13) The composition according to (11) or (12), further comprising a chiral agent.

(14) A cured object, obtained by curing the composition according to any one of (11) to (13).

(15) An optically anisotropic body, obtained by curing the composition according to any one of (11) to (13).

(16) A reflective film, obtained by curing the composition according to any one of (11) to (13).

According to the present invention, it is possible to provide a compound which has high refractive index anisotropy Δn and excellent light resistance and which exhibits liquid crystallinity.

In addition, according to the present invention, it is also possible to provide a composition, a cured object, an optically anisotropic body, and a reflective film which contain the compound.

DESCRIPTION OF THE PREFERRED EMBODIMENTS

Hereinafter, the present invention will be described in detail. In the present specification, a numerical range represented using "to" means a range including numerical values described before and after the preposition "to" as a lower limit value and an upper limit value.

In addition, in the present specification, a "(meth)acryloyl group" is a description representing both an acryloyl group and a methacryloyl group.

As described above, in the compound represented by General Formula (1) of the present invention, desired effects can be obtained by having an amide group at a predetermined position. Details for the reason why such effects can be obtained are unknown. However, it is presumed that due to introduction of an amide group at a position adjacent to a tolan skeleton, a conjugation length becomes longer and Δn is improved. In addition, unlike a compound containing an ester group in the related art, it is presumed that due to introduction of an amide group, Fries rearrangement hardly occurs and light resistance is improved.

(Compound Represented by General Formula (1))

Hereinafter, the compound represented by General Formula (1) will be described in detail.

The compound represented by General Formula (1) shows liquid crystallinity. For a compound to show liquid crystallinity, it is intended that the compound has a property of expressing a mesophase between a crystalline phase (low temperature side) and an isotropic phase (high temperature side) in a case where a temperature is changed. As a specific observation method, optical anisotropy and fluidity derived from a liquid crystalline phase can be confirmed by making an observation under a polarization microscope while heating or lowering a temperature of a compound with a hot stage system FP90, manufactured by Mettler-Toledo International Inc., or the like.

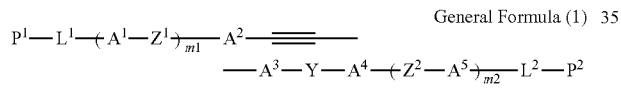

General Formula (1)

In General Formula (1), $P^1$ and $P^2$ each independently represent a hydrogen atom or a substituent, and at least one of $P^1$ or $P^2$ represents a polymerizable group. Among these, from the viewpoint of superior reactivity, both $P^1$ and $P^2$ are preferably polymerizable groups.

A type of the substituent is not particularly limited, and a known substituent is mentioned. As the substituent, for example, a halogen atom, an alkyl group, an alkoxy group, an aryl group, a nitrile group, an isothiocyanate group, a hydroxyl group, an amino group, a carboxyl group, a sulfonamide group, an N-sulfonylamide group, an acyl group, an acyloxy group, and an alkoxycarbonyl group are mentioned. Each of the above groups may be further substituted with a substituent. For example, a hydrogen atom in the alkyl group may be substituted with a fluorine atom. As the substituent, a polymerizable group is preferable.

A type of the polymerizable group is not particularly limited, and a known polymerizable group is mentioned. From the viewpoint of reactivity, a functional group that can be subjected to addition polymerization reaction is preferable, and a polymerizable ethylenically unsaturated group or a cyclic polymerizable group is more preferable. As the polymerizable group, for example, a (meth)acryloyloxy group, a vinyl group, a maleimide group, an acetyl group, a styryl group, an allyl group, an epoxy group, an oxetane group, and a group containing these groups are mentioned. A hydrogen atom in each of the above groups may be substituted with another substituent such as a halogen atom.

As preferable specific examples of the polymerizable group, groups represented by General Formulae (P-1) to (P-19) are mentioned. In the following formulae, *represents a bonding position.

(P-1)

(P-2)

(P-3)

(P-4)

(P-5)

(P-6)

(P-7)

(P-8)

(P-9)

(P-10)

(P-11)

(P-12)

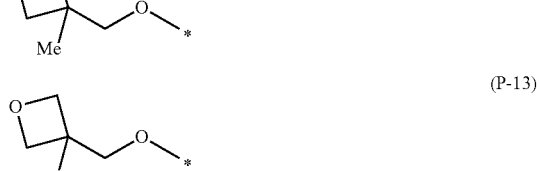

(P-13)

-continued

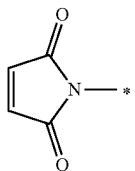 (P-14)

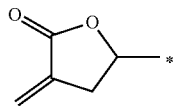 (P-15)

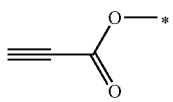 (P-16)

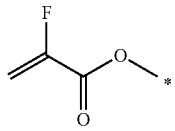 (P-17)

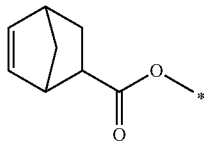 (P-18)

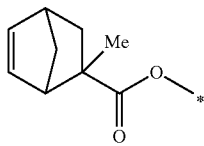 (P-19)

$L^1$ and $L^2$ each independently represent a single bond or a divalent linking group.

The divalent linking group is not particularly limited, and examples thereof include a divalent hydrocarbon group (which may be a divalent saturated hydrocarbon group or a divalent aromatic hydrocarbon group. The divalent saturated hydrocarbon group which may be linear, branched, or cyclic preferably has 1 to 20 carbon atoms, and examples thereof include an alkylene group. In addition, the divalent aromatic hydrocarbon group preferably has 5 to 20 carbon atoms, and examples thereof include a phenylene group. Besides that, the divalent hydrocarbon group may be an alkenylene group or an alkynylene group), a divalent heterocyclic group, —O—, —S—, —SO$_2$—, —NR$^1$—, —CO—(—C(=O)—), —COO—(—C(=O)O—), —NR$^1$—CO—, —CO—NR$^1$—, —SO$_3$—, —SO$_2$NR$^1$—, and a group obtained by combining two or more thereof. Here, W represents a hydrogen atom or an alkyl group (preferably having 1 to 10 carbon atoms).

A hydrogen atom in the divalent linking group may be substituted with another substituent such as a halogen atom.

Among these, from the viewpoint of further improving liquid crystallinity of the compound represented by General Formula (1), it is preferable that $L^1$ is a group represented by General Formula (2), and $L^2$ is a group represented by General Formula (3).

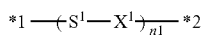 General Formula (2)

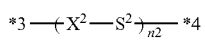 General Formula (3)

In General Formulae (2) and (3), $S^1$ and $S^2$ each independently represent an alkylene group which may contain a heteroatom.

The number of carbon atoms contained in the alkylene group is not particularly limited, and is preferably 1 to 30, more preferably 1 to 20, and even more preferably 1 to 10.

In a case where a heteroatom is contained in the alkylene group, a type of the heteroatom is not particularly limited. Examples thereof include an oxygen atom, a nitrogen atom, a sulfur atom, a selenium atom, and a tellurium atom. Among these, the heteroatom is preferably contained in the alkylene group, in a form of —Y$^1$—, —N(R$^2$)—, —C(=Y$^2$)—, —CON(R$^3$)—, —C(=Y)Y$^4$—, —SO$_t$—, —SO$_2$N(R$^4$)—, or a group obtained by combining these.

$Y^1$ to $Y^4$ each independently represent an oxygen atom, a sulfur atom, a selenium atom, or a tellurium atom. t represents an integer of 1 to 3. $R^2$, $R^3$, and $R^4$ each independently represent a hydrogen atom or an alkyl group.

Among these, $S^1$ and $S^2$ are preferably alkylene groups having 1 to 20 carbon atoms of which one —CH$_2$— or two or more adjacent —CH$_2$—'s each independently may be substituted with —O—, —COO—, —OCO—, or —OCO—O—.

$X^1$ and $X^2$ each independently represent a single bond, —O—, —S—, —OCH$_2$—, —CH$_2$O—, —CO—, —COO—, —OCO—, —CO—S—, —S—CO—, —OCO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, or —C≡C—.

Among these, it is preferable that $X^1$ and $X^2$ are each independently a single bond, —O—, —COO—, or —OCO—.

n1 and n2 each independently represent an integer of 0 to 8. Among these, 0 to 4 is preferable, and 1 is more preferable.

In General Formula (2), *1 represents a bonding position with $P^1$ in General Formula (1), and *2 represents a bonding position with $A^1$ in General Formula (1). In General Formula (3), *3 represents a bonding position with $A^5$ in General Formula (1), and *4 represents a bonding position with $P^2$ in General Formula (I).

$A^1$ to $A^5$ each independently represent an aromatic hydrocarbon ring group or aromatic heterocyclic group which may have a substituent. $A^1$ to $A^5$ are each a divalent group, in other words, a divalent aromatic hydrocarbon ring group or a divalent aromatic heterocyclic group which may have a substituent.

Among these, from the viewpoint of further improving solubility of the compound represented by General Formula (1), an aromatic hydrocarbon ring group having a substituent or an aromatic heterocyclic group having a substituent is preferable. In particular, it is more preferable that at least one of $A^2$, . . . , or $A^4$ is an aromatic hydrocarbon ring group having a substituent or an aromatic heterocyclic group having a substituent, and it is even more preferable that $A^3$ is an aromatic hydrocarbon ring group having a substituent or an aromatic heterocyclic group having a substituent.

The aromatic hydrocarbon ring group may be a monocyclic structure or a polycyclic structure. As specific examples of a ring constituting the aromatic hydrocarbon group, for example, a benzene ring, a biphenyl ring, a naphthalene ring, an anthracene ring, a phenanthrene ring, and a fluorene ring are mentioned. Among these, a benzene ring is preferable.

The aromatic heterocyclic group may be a monocyclic structure or a polycyclic structure. As specific examples of a ring constituting the aromatic heterocyclic group, a furan ring, a thiophene ring, a pyrrole ring, an oxazole ring, an isoxazole ring, an oxadiazole ring, a thiazole ring, an isothiazole ring, a thiadiazole ring, an imidazole ring, a pyrazole ring, a triazole ring, a furazan ring, a tetrazole ring, a pyridine ring, a pyridazine ring, a pyrimidine ring, a pyrazine ring, a triazine ring, a tetrazine ring, and a benzothiazole ring are mentioned.

The aromatic hydrocarbon ring group and the aromatic heterocyclic group may have a substituent. A type of the substituent is not particularly limited, and a known substituent is mentioned. For example, a halogen atom, an alkyl group, an alkoxy group, an aryl group, a hydroxyl group, an amino group, a carboxyl group, a sulfonamide group, an N-sulfonylamide group, an acyl group, an acyloxy group, and an alkoxycarbonyl group are mentioned. Each of the above groups may be further substituted with a substituent. For example, a hydrogen atom in the alkyl group may be substituted with a fluorine atom. In addition, the number of the substituent is not particularly limited, and the aromatic hydrocarbon ring group and the aromatic heterocyclic group may have one substituent or may have a plurality of substituents.

Among these, in view of further improving solubility of the compound represented by General Formula (1), the substituent is preferably a fluorine atom, a chlorine atom, a fluoroalkyl group, an alkoxy group, or an alkyl group, and more preferably a fluoroalkyl group, an alkoxy group, or an alkyl group.

The number of carbon atoms in the fluoroalkyl group and alkyl group, and the number of carbon atoms of the alkyl group in the alkoxy group are not particularly limited, and are preferably 1 to 10, more preferably 1 to 5, and even more preferably 1 to 3, with 1 being particularly preferable.

The fluoroalkyl group is a group in which at least one hydrogen atom in the alkyl group is substituted with a fluorine atom, and is preferably a group in which all hydrogen atoms in the alkyl group are substituted with fluorine atoms (so-called perfluoroalkyl group is preferable).

$Z^1$ and $Z^2$ each independently represent a single bond or a divalent linking group.

Definition and exemplification of the divalent linking group are the same as the definition and exemplification of the divalent linking group represented by $L^1$ and $L^2$ as described above.

Among these, from the viewpoint of exhibiting superior effects of the present invention, it is preferable that $Z^1$ and $Z^2$ each independently represent a single bond, —COO—, —OCO—, —CO—NH—, —NH—CO—, or —C≡C—.

Y represents —CO—NH— or —NH—CO—.

m1 and m2 each independently represent an integer of 0 to 2, and m1+m2 represents an integer of 0 to 2. Among these, from the viewpoint of exhibiting superior effects of the present invention, m1+m2 is preferably 0 or 1.

Refractive index anisotropy Δn of the compound represented by General Formula (1) is not particularly limited. The Δn is preferably 0.23 or more, and more preferably 0.25 or more. An upper limit thereof is not particularly limited, and is 0.60 or less in many cases.

As a method of measuring the Δn, a method using a wedge-shaped liquid crystal cell described on page 202 of the Liquid Crystal Handbook (edited by Liquid Crystal Handbook Editing Committee, published by Maruzen Co., Ltd.) is generally used. In a case of a compound which is liable to crystallize, it is also possible to carry out evaluation with a mixture thereof with other liquid crystals and to estimate Δn from extrapolated values thereof.

The Δn corresponds to a measured value at a wavelength of 550 nm at 30° C.

The compound represented by General Formula (1) can be synthesized by a known method.

As the compound represented by General Formula (1), for example, the following are exemplified.

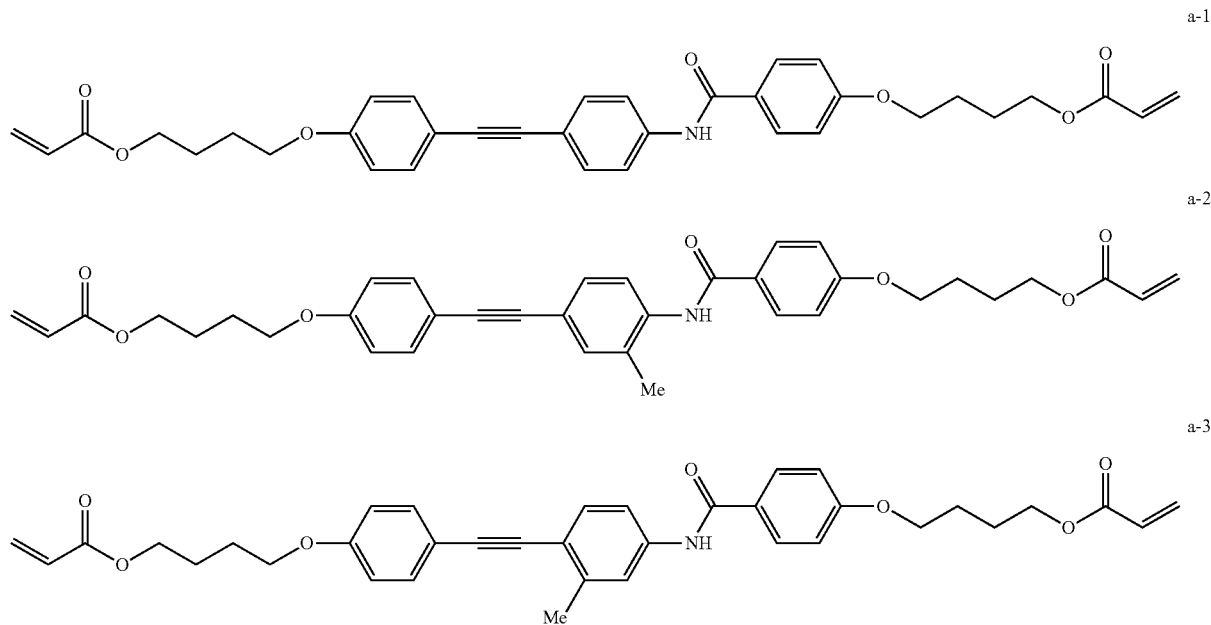

a-4
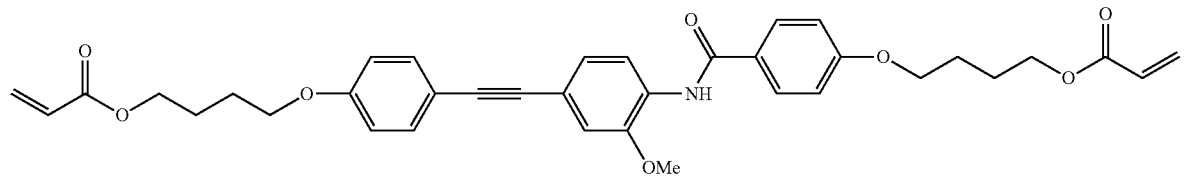
a-5
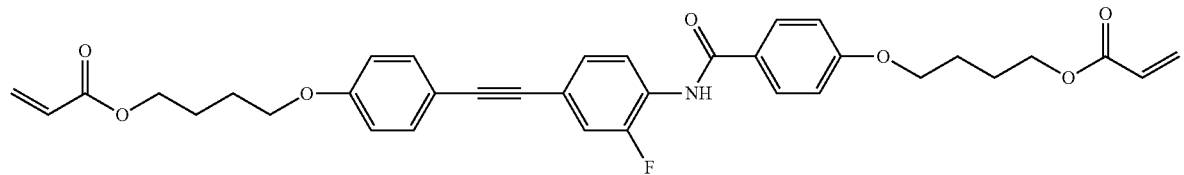
a-6
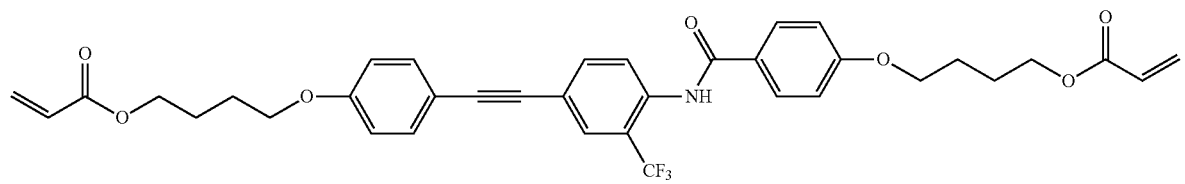
a-7
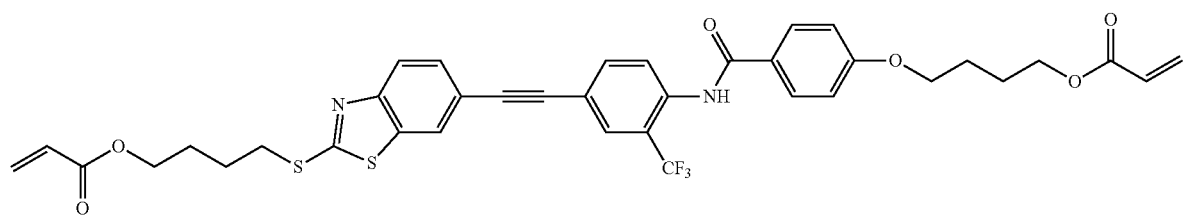
a-8
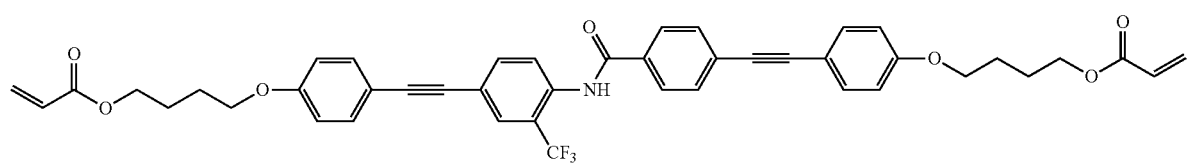
a-9
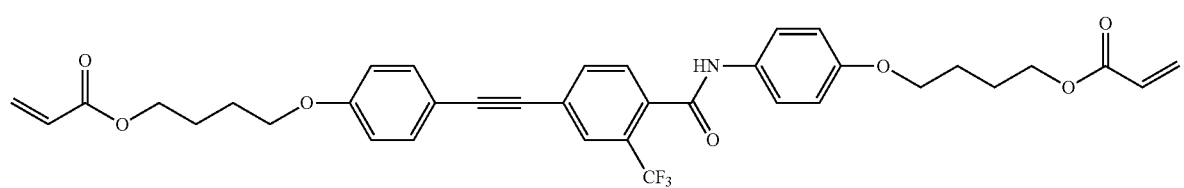
a-10
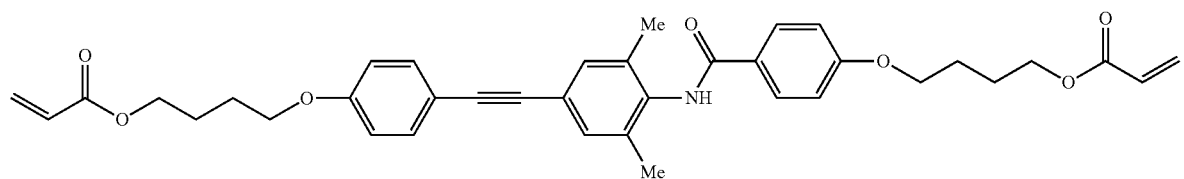

-continued
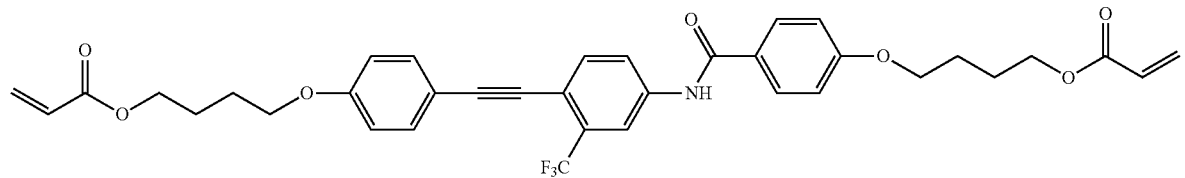
a-11
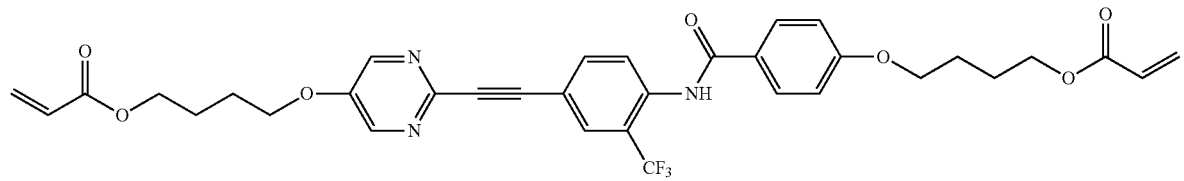
a-12
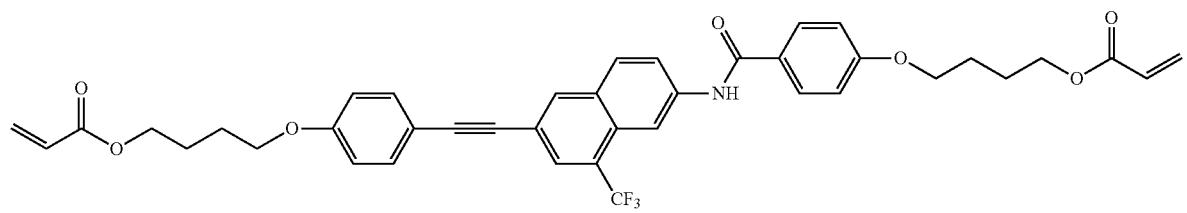
a-13
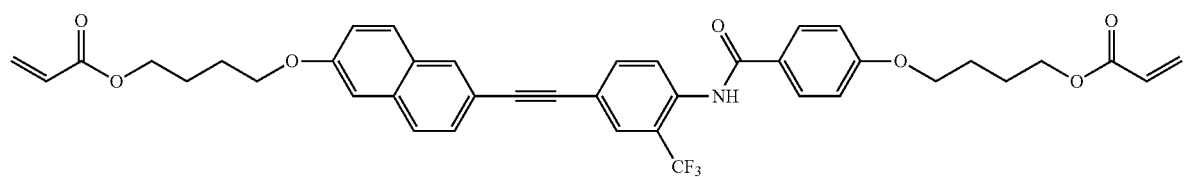
a-14
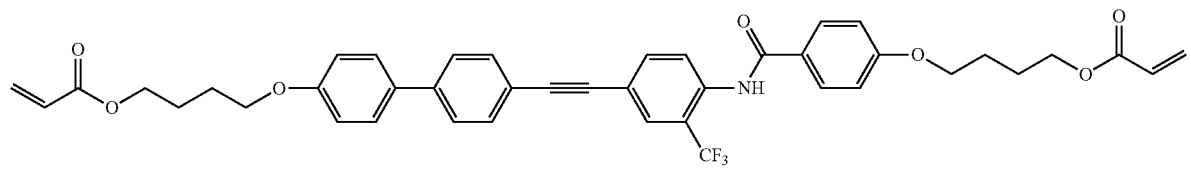
a-15
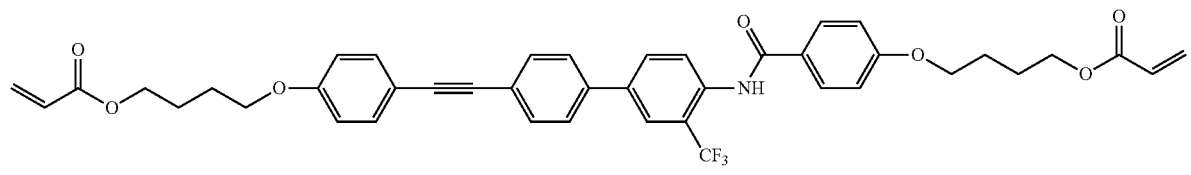
a-16
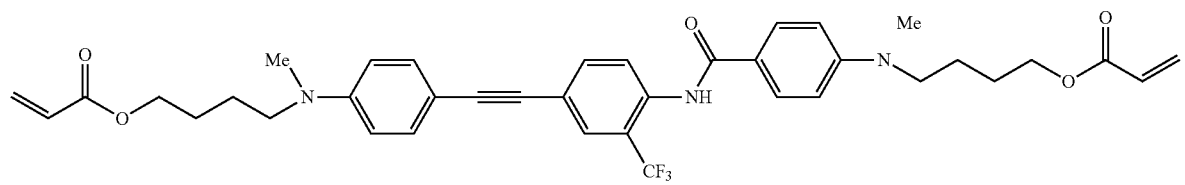
a-17

-continued a-18
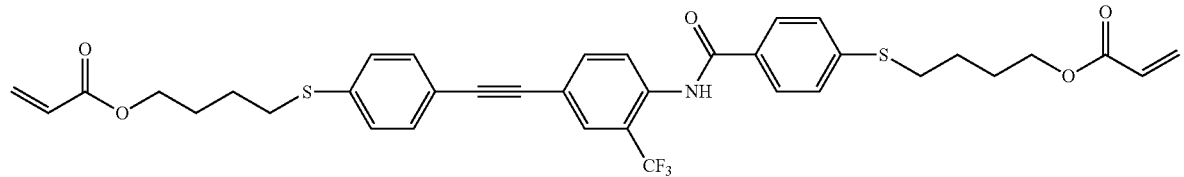

a-19
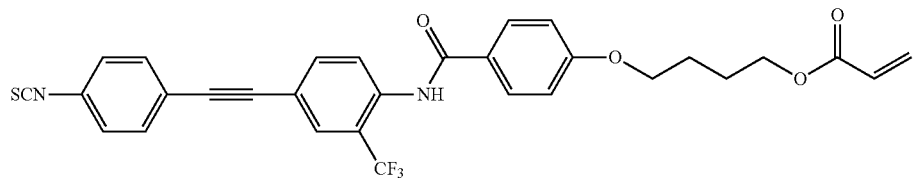

a-20
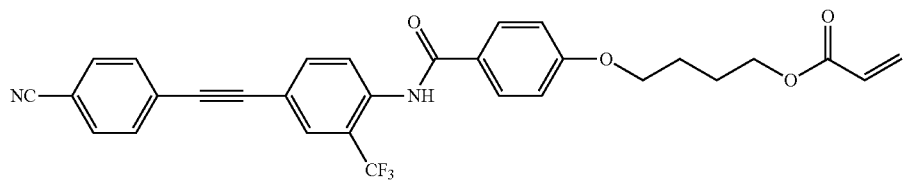

a-21
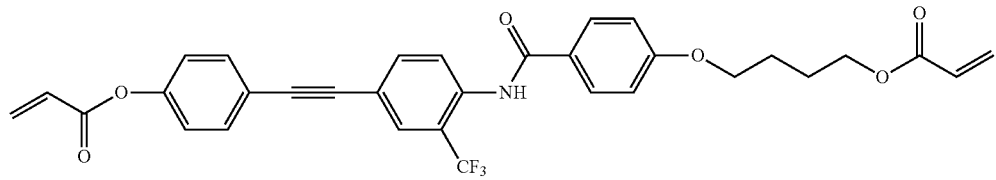

a-22
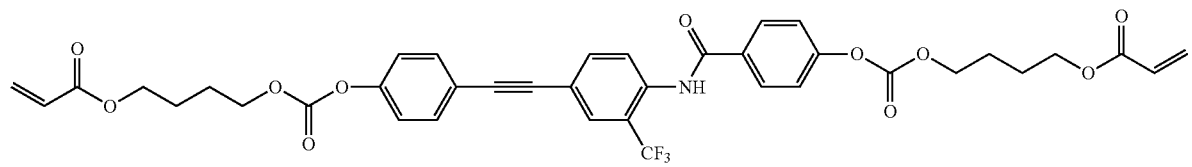

a-23
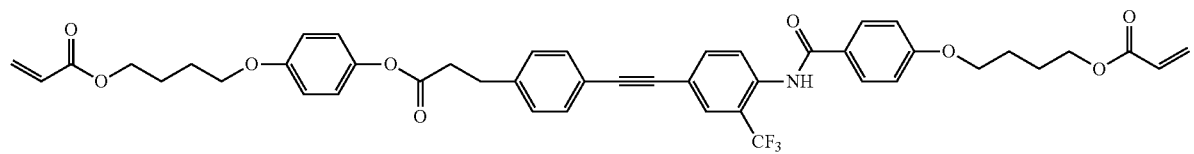

a-24
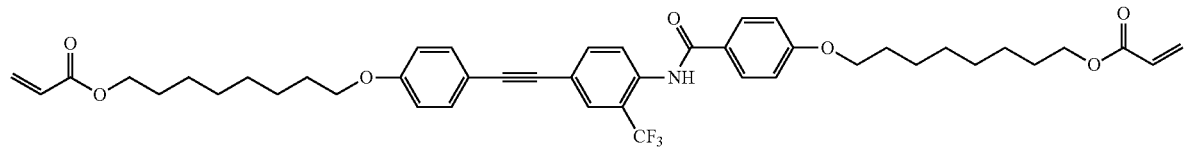

The compound represented by General Formula (1) can be used in the form of a composition containing this compound. Components other than the compound represented by General Formula (1) may be contained in the composition.

Hereinafter, other components contained in the composition will be described in detail.

(Polymerization Initiator)

The composition may contain a polymerization initiator.

The polymerization initiator is preferably a photopolymerization initiator which is capable of initiating a polymerization reaction by ultraviolet irradiation. As the photopolymerization initiator, for example, an α-carbonyl compound, acyloin ether, an α-hydrocarbon-substituted aromatic acyloin compound, a polynuclear quinone compound, a phenazine compound, and an oxadiazole compound are mentioned.

A content of the polymerization initiator in the composition is not particularly limited, and is preferably 0.1% to 20% by mass, and more preferably 1% to 8% by mass, with respect to the entire mass of the compound represented by General Formula (1).

(Chiral Agent)

The composition may contain a chiral agent. In a case where the composition contains the chiral agent, a cholesteric liquid crystalline phase can be formed.

A type of the chiral agent is not particularly limited. The chiral agent may be liquid crystalline or non-liquid crystalline. The chiral agent generally contains an asymmetric carbon atom. However, an axial asymmetric compound or a planar asymmetric compound which does not contain any asymmetric carbon atom can also be used as the chiral agent. As the axial asymmetric compound or the planar asymmetric compound, binaphthyl, helicene, paracyclophane, and derivatives thereof are mentioned. The chiral agent may have a polymerizable group.

Besides the above, the composition may also contain other additives such as a solvent, an alignment control agent, an antioxidant, an ultraviolet absorber, a sensitizer, a stabilizer, a plasticizer, a chain transfer agent, a polymerization inhibitor, an anti-foaming agent, a leveling agent, a thickener, a flame retardant, a surfactant, a dispersant, and a coloring material such as a dye and a pigment.

(Curing Method and Cured Object)

A method of curing (polymerizing and curing) the above composition is not particularly limited, and a known method can be adopted. For example, a form having a step X in which a predetermined substrate and the composition are brought into contact with each other to form a composition layer on the substrate, and a step Y in which the composition layer is subjected to a heat treatment so that the compound represented by General Formula (1) is aligned, and then is subjected to a curing treatment. According to the present form, the compound represented by General Formula (1) can be immobilized in an aligned state, and a layer in which a so-called optically anisotropic body or a cholesteric liquid crystalline phase is immobilized can be formed.

Hereinafter, procedures for the step X and the step Y will be described in detail.

The step X is a step of bringing a predetermined substrate into contact with the composition to form a composition layer on the substrate. A type of the substrate to be used is not particularly limited, and known substrates (for example, a resin substrate, a glass substrate, a ceramic substrate, a semiconductor substrate, and a metal substrate) are mentioned.

A method of bringing the substrate into contact with the composition is not particularly limited, and examples thereof include a method of coating the composition on the substrate and a method of immersing the substrate in the composition.

After bringing the substrate into contact with the composition, if necessary, a drying treatment may be carried out in order to remove a solvent from the composition layer on the substrate.

The step Y is a step of subjecting the composition layer to a heat treatment so that the compound represented by General Formula (1) is aligned, and then subjecting the same to a curing treatment.

By subjecting the composition layer to a heat treatment, the compound represented by General Formula (1) is aligned and a liquid crystalline phase is formed. For example, in a case where a chiral agent is contained in the composition layer, a cholesteric liquid crystalline phase is formed.

A condition for the heat treatment is not particularly limited, and an optimal condition is selected depending on a type of the compound represented by General Formula (1).

A method for the curing treatment is not particularly limited, and a photo-curing treatment and a thermal-curing treatment are mentioned. Among these, a light irradiation treatment is preferable, and an ultraviolet irradiation treatment is more preferable.

For the ultraviolet irradiation, a light source such as an ultraviolet lamp is used.

The cured object obtained by the above treatment corresponds to a layer in which a liquid crystalline phase is immobilized. In particular, in a case where the composition contains a chiral agent, a layer is formed in which a cholesteric liquid crystalline phase is immobilized.

These layers do not need to exhibit liquid crystallinity anymore. More specifically, for example, as a state in which the cholesteric liquid crystalline phase is "immobilized", the most typical and preferable form is a state in which alignment of the compound represented by General Formula (1) which is a cholesteric liquid crystalline phase is retained. More specifically, the state is preferably a state in which within a temperature range of usually 0° C. to 50° C., and, under more severe conditions, −30° C. to 70° C., no fluidity is exhibited in the layer, no changes in alignment form occur due to an external field or an external force, and an immobilized alignment form can be kept in a stable and continuous manner.

A cured object is obtained by subjecting the composition to a curing treatment as described above.

The cured object obtained by curing the composition of the present invention can be applied to various uses, and, for example, an optically anisotropic body and a reflective film are mentioned. In other words, an optically anisotropic body or a reflective film obtained by curing the above composition is mentioned as a suitable form.

The optically anisotropic body is intended to have a substance having optical anisotropy.

In addition, the reflective film corresponds to a layer in which the above-described cholesteric liquid crystalline phase is immobilized, and can reflect light in a predetermined reflection band.

EXAMPLES

Hereinafter, the present invention will be described more specifically with reference to examples. Materials, reagents, proportions, operations, and the like shown in the following examples can be appropriately changed without departing from the gist of the present invention. Accordingly, the scope of the present invention is not limited to the following specific examples.

Synthesis Example 1: Synthesis of Compound a-1

Compound a-1 was synthesized according to the following scheme.

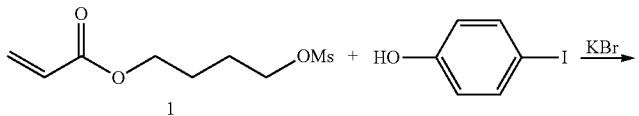

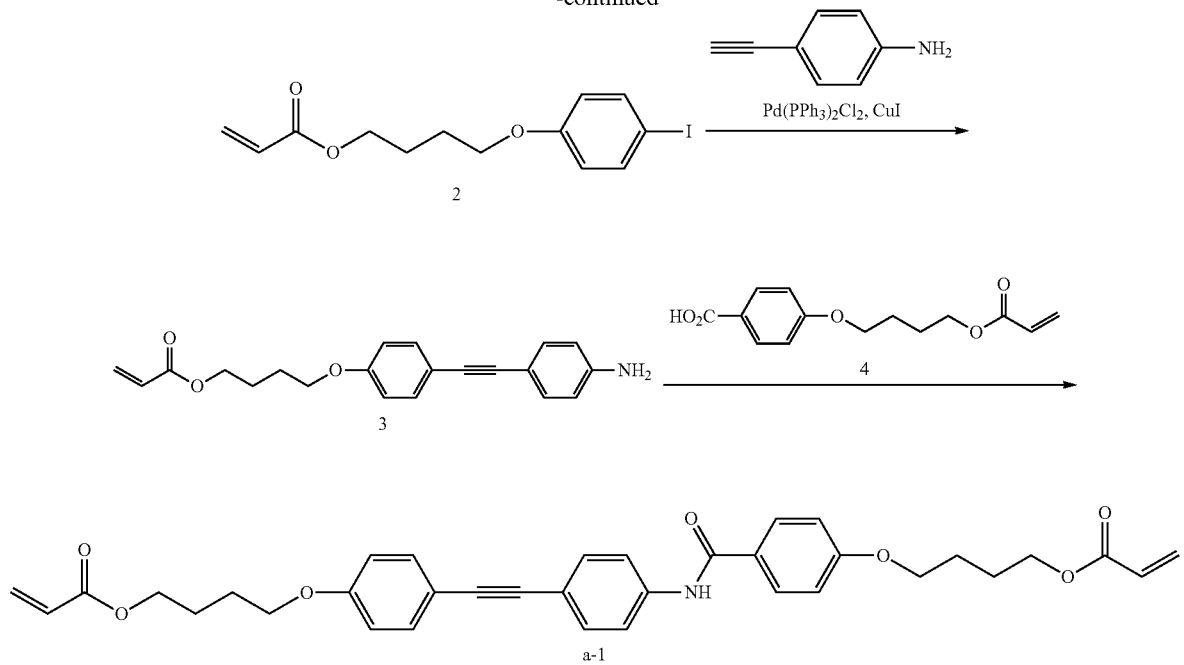

In the above scheme, Compound 1 was synthesized by methanesulfonylating 4-hydroxybutyl acrylate. Compound 4 was synthesized by alkylating 4-hydroxybenzaldehyde with compound 1 and then oxidizing an aldehyde group.

(1) Synthesis of Compound 2

4-Iodophenol (3.99 g, 18.1 mmol) and potassium carbonate (3.78 g, 27.3 mmol) were added to dimethyl acetamide (21 ml). Compound 1 (4.02 g, 18.1 mmol) and potassium iodide (0.508 mmol) were added to the resulting solution, and the solution was stirred at 80° C. for 5 hours. After cooling the solution to room temperature, 1 N hydrochloric acid was added to the solution, followed by extraction with ethyl acetate. The organic layer obtained by extraction was washed once with saline, and magnesium sulfate was added to the washed organic layer. The obtained organic layer was filtered to collect the filtrate, and then the solvent was distilled off from the filtrate under reduced pressure. The resulting residue was purified by flash column chromatography to obtain Compound 2 (4.84 g) as a brown solid.

(2) Synthesis of Compound 3

Under a nitrogen atmosphere, Compound 2 (0.50 g, 1.4 mmol) and 0.26 g (2.2 mmol) of 4-ethenyl aniline were dissolved in a mixed solution of triethylamine (4 ml) and tetrahydrofuran (4 ml). After nitrogen bubbling of the resulting solution was carried out for 30 minutes, Pd(PPh$_3$)$_2$Cl$_2$ (6.3 mg, 9.0 μmol), CuI (4.3 mg, 23 μmol), and PPh$_3$ (14.3 mg, 54.5 μmol) were added to the solution, and the resulting solution was stirred under heating reflux for 2 hours. Next, after the solution was cooled to room temperature, insoluble matters were removed from the solution by filtration, the insoluble matters thus separated were washed with ethyl acetate, and the ethyl acetate used for washing and the filtrate previously obtained were mixed. The resulting solution was washed once with saline, and magnesium sulfate was added to the washed solution. The resulting solution was filtered and the filtrate was collected. Then, the solvent was distilled off from the filtrate under reduced pressure. The resulting residue was purified by flash column chromatography to obtain Compound 3 (0.25 g) as a pale yellow solid.

(3) Synthesis of Compound a-1

Methanesulfonyl chloride (0.775 mmol) and one piece of dibutylhydroxytoluene were dissolved in tetrahydrofuran (2 ml). After cooling the resulting solution to −5° C. or lower, a tetrahydrofuran solution (2 ml) of Compound 4 (0.20 g, 0.76 mmol) and ethyldiisopropylamine (0.15 ml, 0.86 mmol) was added dropwise to the above solution, and the solution was stirred for 1 hour while maintaining a temperature at −5° C. or lower. Next, while maintaining a temperature of the resulting solution at −5° C. or less, a tetrahydrofuran solution (2 ml) of Compound 3 (0.25 g, 0.75 mmol), 1-methylimidazole (1 drop), and ethyl diisopropyl amine (0.15 ml, 0.86 mmol) were added to the solution. Then, the resulting solution was stirred at room temperature for 1 hour. Thereafter, 1 N hydrochloric acid was added to the stirred solution, and then extraction was carried out with ethyl acetate. The organic layer obtained by extraction was washed once with aqueous sodium bicarbonate and once with saline, respectively, and magnesium sulfate was added to the washed organic layer. The obtained organic layer was filtered to collect the filtrate, and then the solvent was distilled off from the filtrate under reduced pressure. The resulting residue was purified by flash column chromatography to obtain Compound a-1 (0.34 g) as a white solid.

$^1$H-nuclear magnetic resonance (NMR) (CDCl$_3$): δ=1.90 (m, 8H), 4.01 (t, 2H), 4.08 (t, 2H), 4.25 (m, 4H), 5.83 (d, 2H), 6.13 (dd, 2H), 6.41 (d, 2H), 6.88 (d, 2H), 6.99 (d, 2H), 7.47 (d, 2H), 7.50 (d, 2H), 7.62 (d, 2H), 7.78 (s, 1H), 7.83 (d, 2H)

Synthesis Example 2: Synthesis of Compound a-2

Compound a-2 was synthesized according to the following scheme.

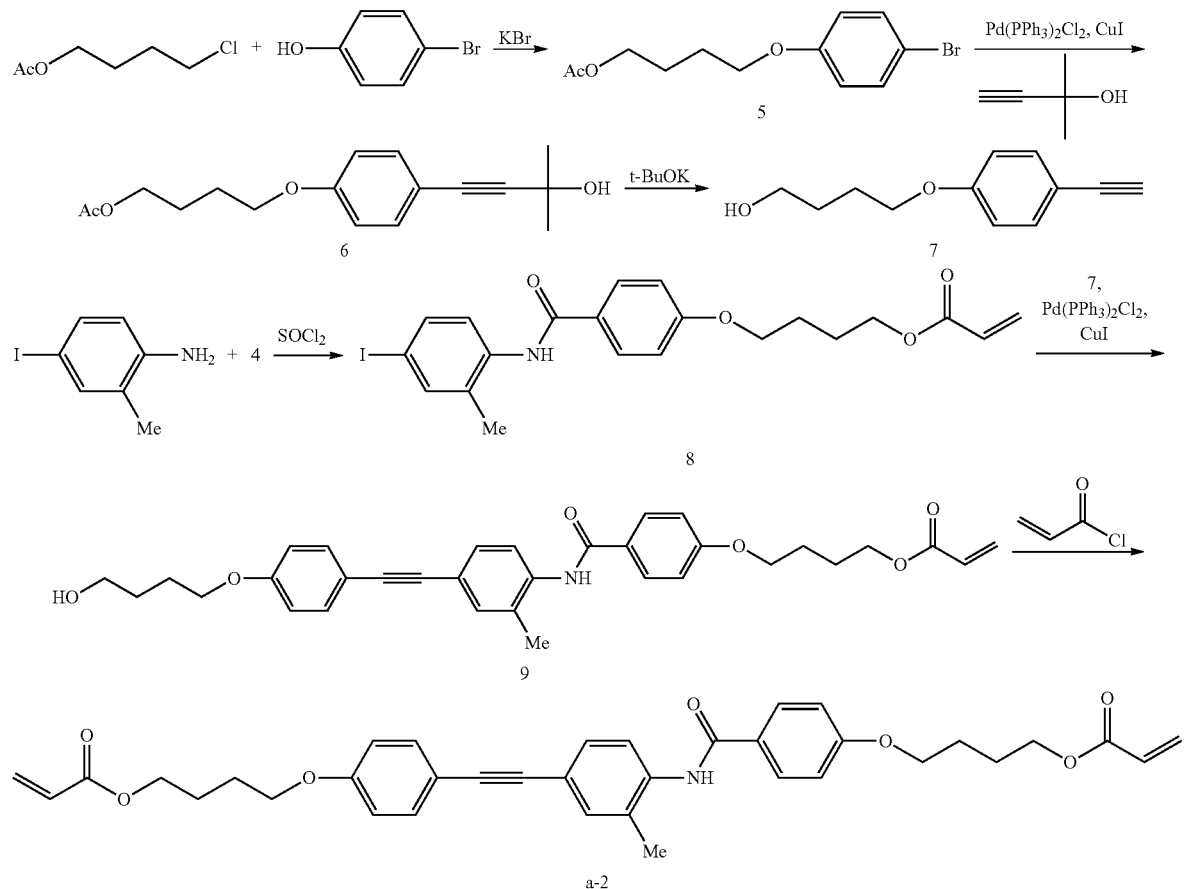

(1) Synthesis of Compound 5

Under a nitrogen atmosphere, 4-bromophenol (170 g, 0.983 mol) was dissolved in dimethyl acetamide (690 ml). Potassium carbonate (163 g, 1.18 mol) and potassium iodide (19.6 g, 0.118 mol) were added to the resulting solution, and a temperature of the solution was elevated to 70° C. Thereafter, 4-chlorobutyl acetate (148 g, 0.983 mol) was added dropwise to the solution, and the solution was stirred at 90° C. for 5 hours. After cooling the solution to room temperature, insoluble matters were removed from the solution by filtration, the insoluble matters thus separated were washed with toluene, and the toluene used for washing and the filtrate previously obtained were mixed. The resulting solution was washed twice with 1 N hydrochloric acid, twice with saline, once with 1 N sodium hydroxide aqueous solution, twice with pure water, and once with saline, respectively. Magnesium sulfate was added to the washed solution. The resulting solution was filtered and the filtrate was collected. Then, the solvent was distilled off from the filtrate under reduced pressure. The resulting residue was purified by flash column chromatography to obtain Compound 5 (249 g) in the form of colorless oil.

(2) Synthesis of Compound 6

Under a nitrogen atmosphere, Compound 5 (240 g, 0.836 mol) and 3-methyl-1-butyn-3-ol (105 g, 1.25 mol) were dissolved in triethylamine (720 ml). After nitrogen bubbling of the resulting solution for 30 minutes, Pd(PPh$_3$)$_2$Cl$_2$ (3.52 g, 5.01 mmol) and CuI (1.59 g, 8.35 mmol) were added to the solution, and the resulting solution was stirred under heating reflux for 4 hours. Thereafter, Pd(PPh$_3$)$_2$Cl$_2$ (1.76 g, 2.51 mmol) and CuI (0.80 g, 4.2 mmol) were further added to the solution and the resulting solution was stirred under heating reflux for 2 hours. After cooling the solution to room temperature, insoluble matters were removed from the solution by filtration, the insoluble matters thus separated were washed with ethyl acetate, and the ethyl acetate used for washing and the filtrate previously obtained were mixed. The resulting solution was washed twice with pure water and once with saline, respectively, and magnesium sulfate was added to the washed solution. The resulting solution was filtered and the filtrate was collected. Then, the solvent was distilled off from the filtrate under reduced pressure. The resulting residue was purified by flash column chromatography to obtain compound 6 (215 g) in the form of a brown oil.

(3) Synthesis of Compound 7

Under a nitrogen atmosphere, Compound 6 (210 g, 0.723 mol) was dissolved in isopropyl alcohol (1,300 ml). Potassium tert-butoxide (284 g, 2.53 mol) was added to the resulting solution and the solution was stirred at 105° C. for 4 hours. After cooling the solution to room temperature, 1 N hydrochloric acid was added to the solution, followed by extraction with ethyl acetate. The organic layer obtained by the extraction was washed twice with pure water and once with saline, respectively, and magnesium sulfate was added to the washed organic layer. The obtained organic layer was filtered to collect the filtrate, and then the solvent was distilled off from the filtrate under reduced pressure. The resulting residue was purified by flash column chromatography to obtain Compound 7 (107 g) as a brown solid.

(4) Synthesis of Compound 8

Compound 4 (5.67 g, 21.5 mmol) and dibutylhydroxytoluene (10 mg, 45 μmol) were dissolved in a mixed solution of toluene (10 ml) and dimethyl acetamide (10 ml). Thionyl chloride (1.50 ml, 20.7 mmol) was added dropwise to the resulting solution under ice cooling, and the solution was stirred at room temperature for 4 hours. Furthermore, a dimethyl acetamide solution (10 ml) of 4-iodo-2-methylaniline (2.00 g, 8.58 mmol) was added dropwise to the resulting solution under ice cooling, and the solution was stirred at 80° C. for 2 hours. After cooling the solution to room temperature, 1 N hydrochloric acid was added to the solution, followed by extraction with ethyl acetate. The organic layer obtained by the extraction was washed once with aqueous sodium bicarbonate and once with saline, respectively, and sodium sulfate was added to the washed organic layer. The obtained organic layer was filtered to collect the filtrate, and then the solvent was distilled off from the filtrate under reduced pressure. The resulting residue was purified by flash column chromatography to obtain Compound 8 (3.17 g) as a white solid.

(5) Synthesis of Compound 9

Under a nitrogen atmosphere, Compound 7 (0.66 g, 3.5 mmol) and Compound 8 (1.50 g, 3.13 mmol) were dissolved in a mixed solution of tetrahydrofuran (20 ml) and triethylamine (2 ml). After nitrogen bubbling of the resulting solution for 30 minutes, Pd(PPh$_3$)$_2$Cl$_2$ (112 mg, 0.159 mmol) and CuI (61.0 mg, 0.320 mmol) were added to the solution, and the solution was stirred at 55° C. for 2 hours. After cooling the solution to room temperature, insoluble matters were removed from the solution by filtration, the insoluble matters thus separated were washed with ethyl acetate, and the ethyl acetate used for washing and the filtrate previously obtained were mixed. The resulting solution was washed once with a saturated aqueous solution of ammonium chloride, once with pure water, and once with saline, respectively. Sodium sulfate was added to the washed solution. The resulting solution was filtered and the filtrate was collected. Then, the solvent was distilled off from the filtrate under reduced pressure. The resulting residue was purified by flash column chromatography to obtain Compound 9 (1.70 g) as a brown solid.

(6) Synthesis of Compound a-2

Compound 9 (1.70 g, 3.14 mmol) was dissolved in dimethyl acetamide (15 ml). Acryl chloride (0.31 ml, 3.8 mmol) was added to the resulting solution under ice cooling, and the solution was stirred at room temperature for 2 hours. Furthermore, acryl chloride (0.31 ml, 3.8 mmol) was added to the resulting solution under ice cooling, and the solution was stirred at room temperature for 2 hours. Next, 1 N hydrochloric acid was added to the solution, and then the mixture was extracted with ethyl acetate. The organic layer obtained by extraction was washed once with saline, and sodium sulfate was added to the washed organic layer. The obtained organic layer was filtered to collect the filtrate, and then the solvent was distilled off from the filtrate under reduced pressure. The resulting residue was purified by flash column chromatography to obtain Compound a-2 (0.75 g) as a white solid.

$^1$H-NMR (CDCl$_3$): δ=1.88 (m, 8H), 2.29 (s, 3H), 4.01 (t, 2H), 4.09 (t, 2H), 4.26 (m, 4H), 5.82 (dt, 2H), 6.11 (dd, 2H), 6.38 (dt, 2H), 6.84 (d, 2H), 6.99 (d, 2H) 7.35-7.49 (m, 4H), 7.61 (s, 1H), 7.82 (d, 2H), 8.09 (d, 1H)

Synthesis Example 3: Synthesis of Compound a-3

Compound a-3 (0.73 g) was obtained as a white solid according to the same procedure as in Synthesis Example 2, except that 4-iodo-3-methylaniline was used in place of 4-iodo-2-methylaniline.

$^1$H-NMR (CDCl$_3$): δ=1.89 (m, 8H), 2.48 (s, 3H) 4.01 (t, 2H), 4.08 (t, 2H), 4.23 (m, 4H), 5.86 (d, 2H), 6.12 (dd, 2H), 6.40 (d, 2H), 6.87 (d, 2H), 6.99 (d, 2H) 7.40-7.49 (m, 3H), 7.59 (s, 1H), 7.89 (s, 1H), 7.81 (d, 2H)

Synthesis Example 4: Synthesis of Compound a-4

Compound a-4 (0.70 g) was obtained as a white solid according to the same procedure as in Synthesis Example 2, except that 4-iodo-2-methoxyaniline was used in place of 4-iodo-2-methylaniline.

$^1$H-NMR (CDCl$_3$): δ=1.89 (m, 8H), 3.89 (s, 3H), 4.02 (t, 2H), 4.08 (t, 2H), 4.25 (m, 4H), 5.81 (dt, 2H), 6.11 (dd, 2H), 6.39 (dt, 2H), 6.85 (d, 2H), 6.98 (d, 2H), 7.05 (s, 1H), 7.19 (d, 1H), 7.44 (d, 2H), 7.85 (d, 2H), 8.59 (d, 1H), 8.60 (s, 1H)

Synthesis Example 5: Synthesis of Compound a-5

Compound a-5 (0.73 g) was obtained as a white solid according to the same procedure as in Synthesis Example 2, except that 2-fluoro-4-iodoaniline was used in place of 4-iodo-2-methylaniline.

$^1$H-NMR (CDCl$_3$): δ=1.90 (m, 8H), 4.00 (t, 2H), 4.08 (t, 2H), 4.26 (m, 4H), 5.79 (dt, 2H), 6.10 (dd, 2H), 6.38 (dt, 2H), 6.84 (d, 2H), 6.98 (d, 2H), 7.27 (d, 1H) 7.31 (d, 1H), 7.42 (d, 2H), 7.82 (d, 2H), 8.00 (s, 1H), 8.49 (t, 1H)

Synthesis Example 6: Synthesis of Compound a-6

Compound a-6 (11.2 g) was obtained as a white solid according to the same procedure as in Synthesis Example 2, except that 4-iodo-2-trifluoromethylaniline was used in place of 4-iodo-2-methylaniline.

$^1$H-NMR (CDCl$_3$): δ=1.89 (m, 8H), 4.00 (t, 2H), 4.09 (t, 2H), 4.21 (m, 4H), 5.80 (dt, 2H), 6.10 (dd, 2H), 6.39 (dt, 2H), 6.86 (d, 2H), 6.97 (d, 2H), 7.43 (d, 2H) 7.70 (dd, 1H), 7.79 (d, 1H), 7.80 (d, 2H), 8.20 (s, 1H), 8.50 (d, 2H)

Synthesis Example 7: Synthesis of Compound a-7

Compound a-7 was synthesized according to the following scheme.

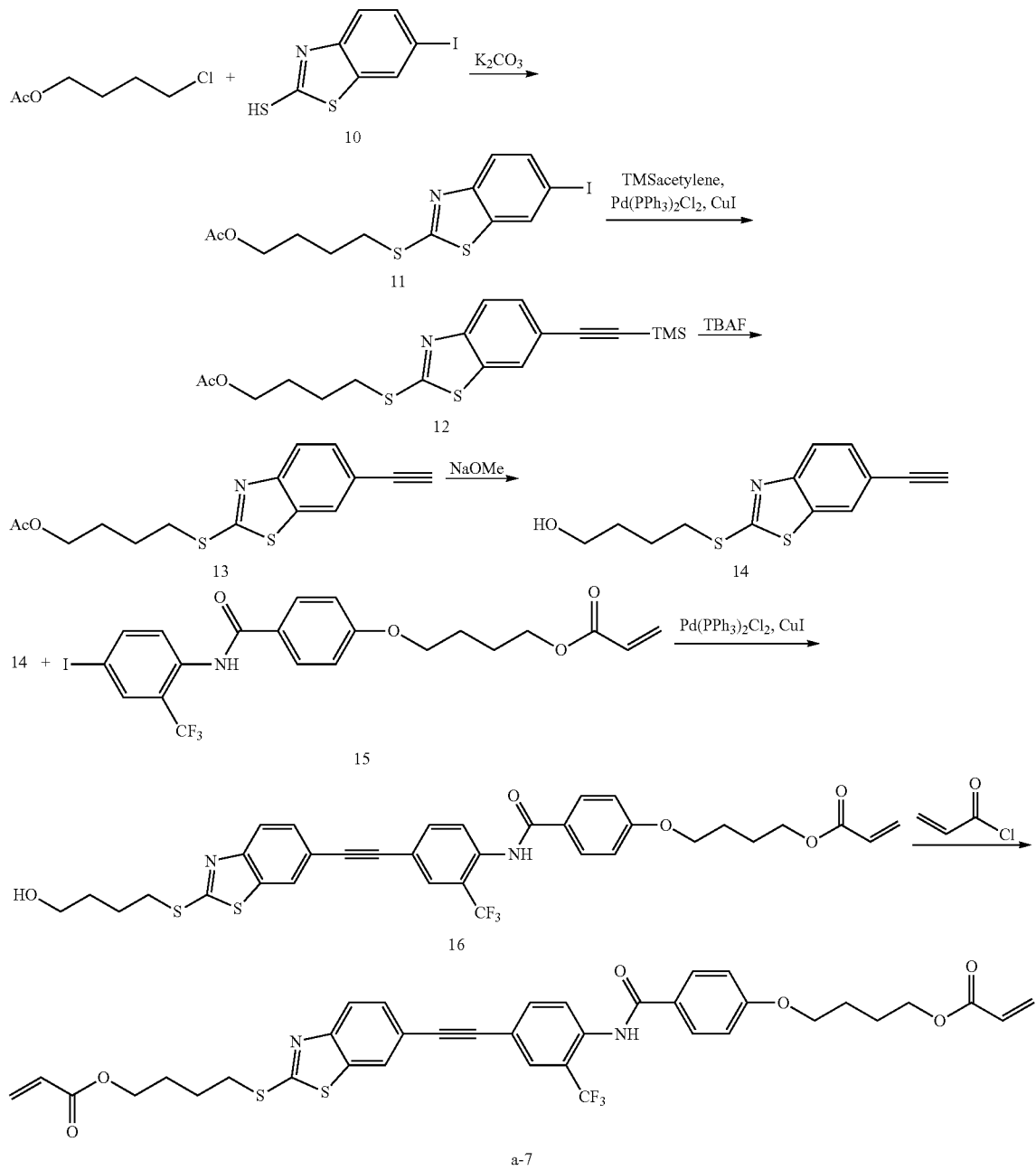

In the above scheme, Compound 10 was synthesized by reacting potassium ethyl xanthate with 2-fluoro-4-iodoaniline.

(1) Synthesis of Compound 11

Compound 10 (0.40 g, 1.4 mmol) and 4-chlorobutyl acetate (0.25 g, 1.7 mmol) were dissolved in dimethyl acetamide (10 ml). Potassium carbonate (0.24 g, 1.7 mmol) and potassium iodide (47.5 mg, 0.286 mmol) were added to the resulting solution, and then the solution was stirred at 70° C. for 6 hours. After cooling the solution to room temperature, 1 N hydrochloric acid was added to the solution, followed by extraction with ethyl acetate. The organic layer obtained by extraction was washed once with saline, and sodium sulfate was added to the washed organic layer. The obtained organic layer was filtered to collect the filtrate, and then the solvent was distilled off from the filtrate under reduced pressure. The resulting residue was purified by flash column chromatography to obtain Compound 11 (0.49 g) in the form of a pale yellow oil.

(2) Synthesis of Compound 12

Under a nitrogen atmosphere, Compound 11 (1.04 g, 2.55 mmol) and trimethylsilyl acetylene (0.54 ml, 5.5 mmol)

were dissolved in a mixed solution of tetrahydrofuran (20 ml) and triethylamine (3 ml). After nitrogen bubbling of the resulting solution for 30 minutes, Pd(PPh$_3$)$_2$Cl$_2$ (89.2 mg, 0.127 mmol) and CuI (48.6 mg, 0.255 mmol) were added to the solution, and the solution was stirred at 55° C. for 2 hours. After cooling the solution to room temperature, insoluble matters were removed from the solution by filtration, the insoluble matters thus separated were washed with ethyl acetate, and the ethyl acetate used for washing and the filtrate previously obtained were mixed. The resulting solution was washed once with a saturated aqueous solution of ammonium chloride and once with saline, respectively. Sodium sulfate was added to the washed solution. The resulting solution was filtered and the filtrate was collected. Then, the solvent was distilled off from the filtrate under reduced pressure. The resulting residue was purified by flash column chromatography to obtain Compound 12 (0.75 g) in the form of a yellow oil.

(3) Synthesis of Compound 13

Compound 12 (0.75 g, 2.0 mmol) was dissolved in tetrahydrofuran (10 ml). A 1 M solution of tetrabutylammonium fluoride in tetrahydrofuran (2.2 ml, 2.2 mmol) was added to the resulting solution, and the solution was stirred at room temperature for 1 hour. To the resulting solution was added 1 N hydrochloric acid, and then extracted with ethyl acetate. The organic layer obtained by extraction was washed once with saline, and sodium sulfate was added to the washed organic layer. The obtained organic layer was filtered to collect the filtrate, and then the solvent was distilled off from the filtrate under reduced pressure. The residue was purified by flash column chromatography to obtain Compound 13 (0.40 g) as pale yellow oil.

(4) Synthesis of Compound 14

Compound 13 (0.40 g, 1.3 mmol) was dissolved in methanol (10 ml). A 28% methanol solution of sodium methoxide (0.04 ml, 0.3 mmol) was added to the resulting solution, and the solution was stirred at room temperature for 1 hour. To the resulting solution was added 1 N hydrochloric acid, and then extracted with ethyl acetate. The organic layer obtained by extraction was washed once with saline, and sodium sulfate was added to the washed organic layer. The obtained organic layer was filtered to collect the filtrate, and then the solvent was distilled off from the filtrate under reduced pressure. The resulting residue was purified by flash column chromatography to obtain Compound 14 (0.34 g) as a pale green solid.

(5) Synthesis of Compound 16

Under a nitrogen atmosphere, Compound 15 (0.64 g, 1.2 mmol) and Compound 14 (0.34 g, 1.3 mmol) were dissolved in a mixed solution of tetrahydrofuran (20 ml) and triethylamine (3 ml). After nitrogen bubbling of the resulting solution for 30 minutes, Pd(PPh$_3$)$_2$Cl$_2$ (43.4 mg, 61.8 μmol) and CuI (48.6 mg, 0.131 mmol) were added to the solution, and the solution was stirred at 55° C. for 1 hour. After cooling the solution to room temperature, insoluble matters were removed from the solution by filtration, the insoluble matters thus separated were washed with ethyl acetate, and the ethyl acetate used for washing and the filtrate previously obtained were mixed. The resulting solution was washed once with a saturated aqueous solution of ammonium chloride and once with saline, respectively. Sodium sulfate was added to the solution after washing. The resulting solution was filtered and the filtrate was collected. Then, the solvent was distilled off from the filtrate under reduced pressure. The resulting residue was purified by flash column chromatography to obtain Compound 16 (0.60 g) as a pale yellow solid.

(6) Synthesis of Compound a-7

Compound 16 (0.60 g, 0.90 mmol) was dissolved in dimethyl acetamide (10 ml). Acryl chloride (0.10 ml, 1.2 mmol) was added to the resulting solution under ice cooling, and the solution was stirred at room temperature for 2 hours. Furthermore, acryl chloride (0.10 ml, 1.2 mmol) was added to the resulting solution under ice cooling, and the solution was stirred at room temperature for 2 hours. To the resulting solution was added 1 N hydrochloric acid, and then extracted with ethyl acetate. The organic layer obtained by extraction was washed once with saline, and sodium sulfate was added to the washed organic layer. The obtained organic layer was filtered to collect the filtrate, and then the solvent was distilled off from the filtrate under reduced pressure. The resulting residue was purified by flash column chromatography to obtain Compound a-7 (0.33 g) as a white solid.

$^1$H-NMR (CDCl$_3$): δ=1.89 (m, 8H), 3.39 (t, 2H), 4.08 (t, 2H), 4.23 (m, 4H), 5.82 (dt, 2H), 6.10 (ddd, 2H), 6.38 (dt, 2H), 6.98 (d, 2H), 7.57 (d, 1H), 7.72 (d, 1H) 7.89-7.99 (m, 4H), 7.93 (s, 1H), 8.21 (s, 1H), 8.55 (d, 1H)

Synthesis Example 8: Synthesis of Compound a-8

Compound a-8 was synthesized according to the following scheme.

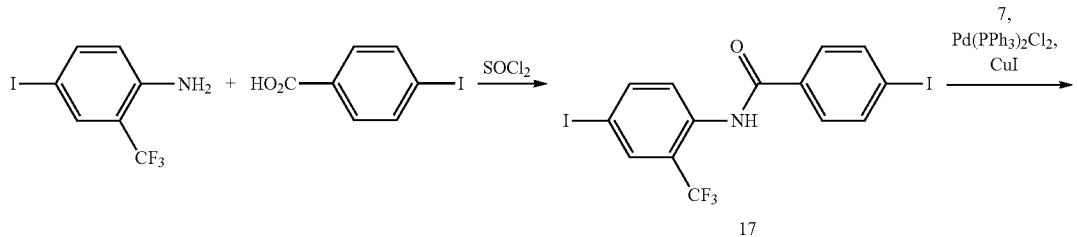

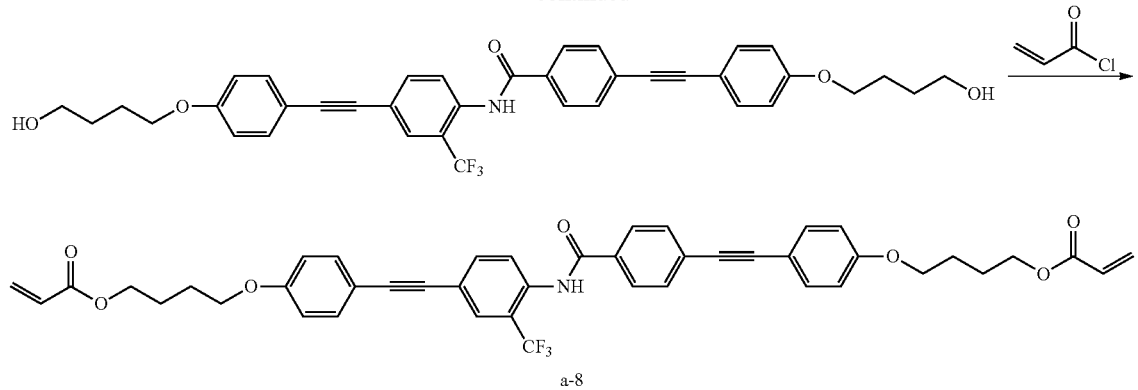

a-8

(1) Synthesis of Compound 17

4-Iodobenzoic acid (2.07 g, 7.21 mmol) was dissolved in toluene (10 ml) and dimethyl acetamide (4 ml). Thionyl chloride (0.66 ml, 9.1 mmol) was added dropwise to the resulting solution under ice cooling, and the solution was stirred at 90° C. for 2 hours. After cooling the solution to room temperature, a solution of 4-iodo-2-trifluoromethyl-aniline (1.42 g, 4.95 mmol) in dimethyl acetamide (10 ml) was added dropwise to the resulting solution, and the solution was stirred at 80° C. for 2 hours. After cooling the solution to room temperature, 1 N hydrochloric acid was added to the solution, followed by extraction with ethyl acetate. The organic layer obtained by extraction was washed once with aqueous sodium bicarbonate, and the solvent was distilled off under reduced pressure.

The resulting residue was dissolved in dimethylformamide, a mixed solution of water and methanol was added to the resulting solution, and a reprecipitation treatment was carried out to obtain Compound 17 (0.98 g) as a white solid.

(2) Synthesis of Compound 18

Under a nitrogen atmosphere, Compound 7 (0.76 g, 4.0 mmol) and Compound 17 (0.98 g, 1.9 mmol) were dissolved in a mixed solution of dimethylformamide (20 ml) and triethylamine (3 ml). After nitrogen bubbling of the resulting solution for 30 minutes, $Pd(PPh_3)_2Cl_2$ (66.9 mg, 95.3 μmol) and CuI (36.7 mg, 0.193 mmol) were added to the solution, and the solution was stirred at 55° C. for 4 hours. After cooling the solution to room temperature, water and methanol were added to the solution, and the precipitate was collected by filtration to obtain Compound 18 (1.06 g) as a brown solid.

(3) Synthesis of Compound a-8

Compound 18 (1.06 g, 1.65 mmol) was dissolved in dimethyl acetamide (25 ml). Acryl chloride (0.33 ml, 4.1 mmol) was added to the resulting solution under ice cooling, and the solution was stirred at room temperature for 3 hours. Thereafter, acryl chloride (0.33 ml, 4.1 mmol) was added to the resulting solution under ice cooling, and the solution was stirred at room temperature for 2 hours. To the resulting solution was added 1 N hydrochloric acid, and then extracted with ethyl acetate. The organic layer obtained by extraction was washed once with saline, and sodium sulfate was added to the washed organic layer. The obtained organic layer was filtered to collect the filtrate, and then the solvent was distilled off from the filtrate under reduced pressure. The resulting residue was purified by flash column chromatography to obtain Compound a-8 (0.65 g) as a white solid.

$^1$H-NMR (CDCl$_3$): δ=1.84 (m, 8H), 4.00 (m, 4H), 4.21 (m, 4H), 5.82 (d, 2H), 6.09 (dd, 2H), 6.39 (d, 2H), 6.86 (d, 2H), 6.89 (d, 2H), 7.41 (d, 2H), 7.46 (d, 2H) 7.62 (d, 2H), 7.71 (d, 1H), 7.80 (d, 2H), 7.83 (d, 2H), 8.28 (s, 1H), 8.49 (d, 1H)

In addition, as described in U.S. Pat. No. 6,514,578B, Compound b-1 as described later was synthesized.

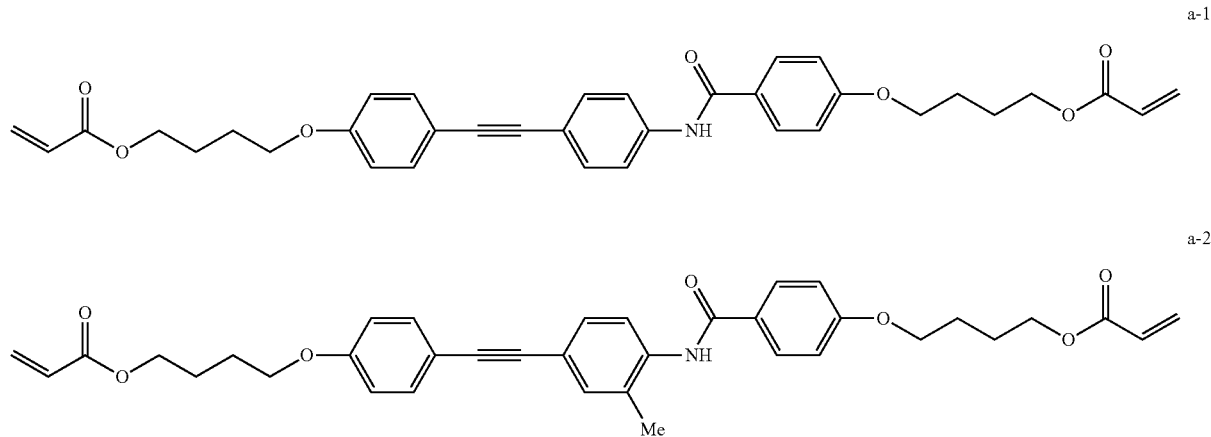

-continued

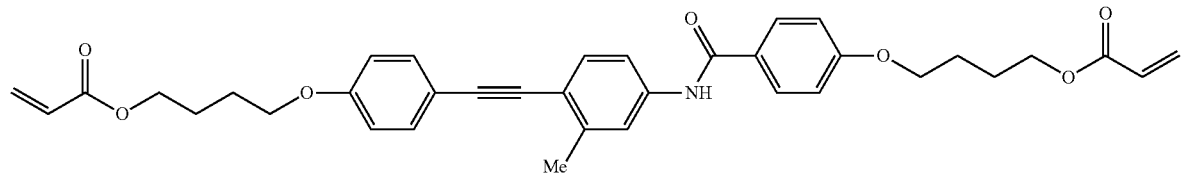
a-3

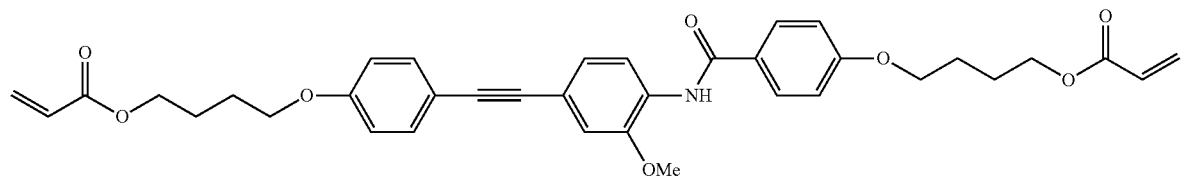
a-4

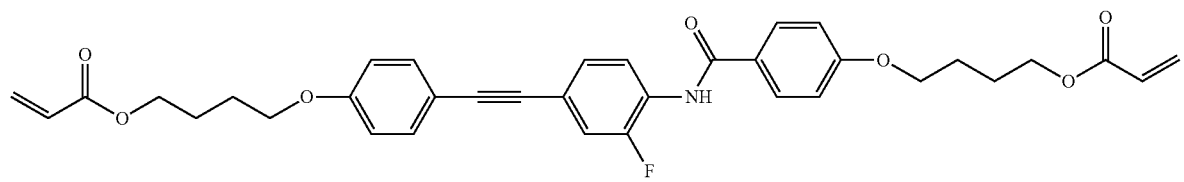
a-5

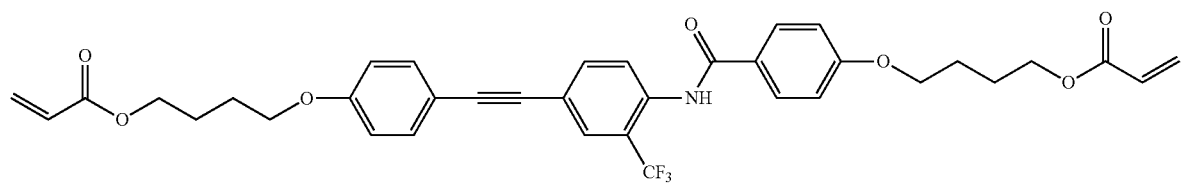
a-6

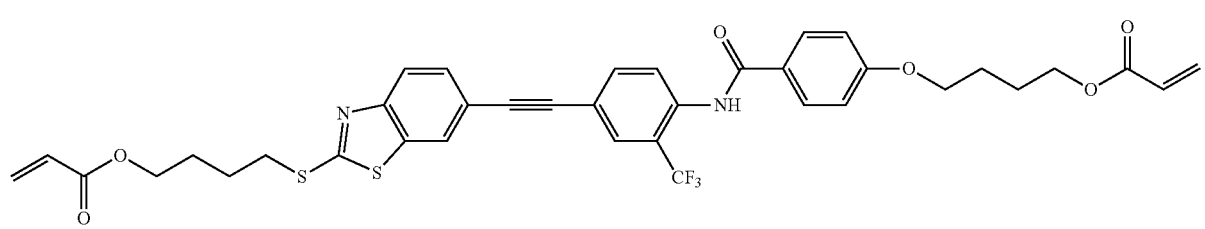
a-7

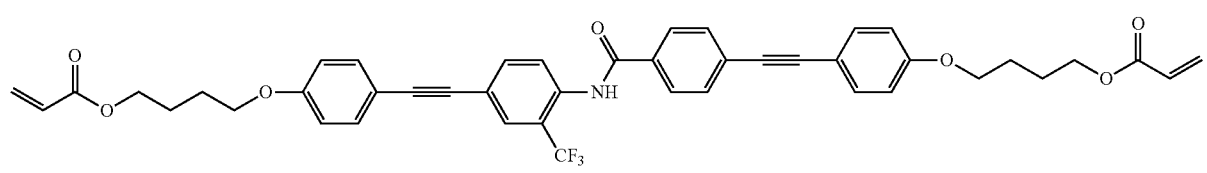
a-8

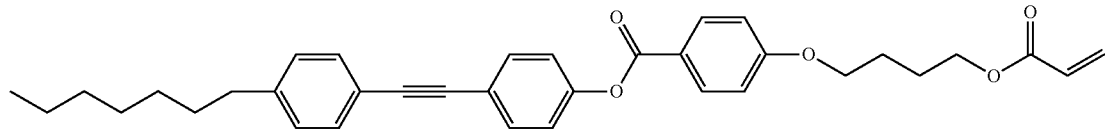
b-1

<Various Evaluations>

Using above-mentioned Compounds a-1 to a-8 and Compound b-1, the following various evaluations were carried out.

(Phase Transition Temperature Measurement)

Each of the compounds was heated on a hot stage and observed under a polarizing microscope to investigate phase transition behavior. The results are shown in Table 1. In the table, "Cr", "Ne", "Iso", and "X" represent a crystalline state, a nematic phase, an isotropic liquid, and an undetermined liquid crystalline phase, respectively.

(Δn (Refractive Index Anisotropy) Measurement)

Δn of each of the compounds was measured by a method using a wedge-shaped liquid crystal cell described on page 202 of the Liquid Crystal Handbook (edited by Liquid Crystal Handbook Editing Committee, published by Maruzen Co., Ltd.). In a case of the compound which is liable to crystallize, evaluation with a mixture thereof with other liquid crystals was carried out and Δn was estimated from extrapolated values thereof. The results are shown in Table 1. The values in the table represent Δn's at 550 nm and 30° C.

(Solubility Measurement)

Ethyl methyl ketone was added dropwise to each of the compounds, and a concentration (% by mass) of the compound in the obtained ethyl methyl ketone solution in a case where the compound was completely dissolved in the solution was measured as "solubility". It is intended that a higher numerical value of solubility indicates excellent solubility in ethyl methyl ketone. The results are shown in Table 1.

(Evaluation of Light Resistance)

Each (5 mg) of the compounds was dissolved in acetonitrile (20 ml), sealed in a 1 cm quartz cell, and the quartz cell was irradiated with ultraviolet light under a condition of 3 J/cm$^2$ using EXECURE 3000-W manufactured by HOYA-SCHOTT CORPORATION, so that a residual rate of each compound was measured. Amounts (masses) of each compound before and after light irradiation were calculated using liquid chromatography. The results are shown in Table 1. In Table 1, "A" represents a residual rate of equal to or greater than 80%, "B" represents a residual rate of equal to or greater than 50% and less than 80%, and "C" represents a residual rate of less than 50%.

The residual rate is a ratio of an amount (mass) of a compound after light irradiation to an amount (mass) of the compound before light irradiation, and can be calculated by the following expression.

Residual rate (%)=(amount of compound after light irradiation/amount of compound before light irradiation)×100

TABLE 1

| | Type of compound | Phase transition temperature | Δn | Light resistance evaluation | Solubility (% by mass) |
|---|---|---|---|---|---|
| Example 1 | Compound a-1 | Cr 147 (132) Ne 178 Iso | 0.289 | A | 5 |
| Example 2 | Compound a-2 | Cr 127 (102 × 109) Ne 140 Iso | 0.280 | A | 23 |
| Example 3 | Compound a-3 | Cr 123 (82) Ne 133 Iso | 0.282 | A | 19 |
| Example 4 | Compound a-4 | Cr 103 (84) Ne 106 Iso | 0.301 | A | 20 |
| Example 5 | Compound a-5 | Cr 86 (60) Ne 160 Iso | 0.278 | A | 11 |
| Example 6 | Compound a-6 | Cr 81 (<-50) Ne 133 Iso | 0.287 | A | 38 |
| Example 7 | Compound a-7 | Cr (68 Ne 84) 94 Iso | 0.304 | A | 22 |
| Example 8 | Compound a-8 | Cr 105 (76) Ne 228 Iso | 0.370 | A | 22 |
| Comparative Example 1 | Compound b-1 | Cr 80 Ne 158 Iso | 0.220 | C | — |

In Table 1, in the phase transition temperature column, numerical values in parenthesis represent crystallization temperatures during temperature lowering.

In addition, for example, "Cr 147 (132) Ne 178 Iso" of Example 1 represents that a phase transition temperature from a crystalline state to a nematic phase is 147° C., and a phase transition temperature from a nematic phase to an isotropic liquid is 178° C.

In addition, for contents in parentheses in "Cr 127 (102 X 109) Ne 140 Iso" in Example 2, it is intended that during temperature lowering, a phase transition from a nematic phase to an X phase (undetermined) occurs at 109° C., and a phase transition from the X phase to a crystalline state occurs at 102° C.

In addition, for (<-50) in Example 6, it is intended that a crystallization temperature during temperature lowering is less than −50° C.

Furthermore, for "Cr (68 Ne 84) 94 Iso" in Example 7, it is intended that no liquid crystalline phase is exhibited during temperature elevation and a phase transition from a crystalline state to an isotropic liquid occurs at 94° C., whereas, during temperature lowering, a phase transition from the isotropic liquid to a nematic phase occurs at 84° C. and a phase transition from the nematic phase to a crystalline state occurs at 68° C.

As shown in Table 1, it was confirmed that all compounds of the present invention exhibited a nematic phase, and exhibited high Δn and excellent light resistance.

In addition, from comparison between Example 1 and other examples, it was confirmed that improved solubility is exhibited in a case where A$^3$ in General Formula (1) is an aromatic hydrocarbon ring group having a substituent. In particular, further increased solubility was exhibited in a case where the substituent was a trifluoromethyl group.

What is claimed is:

1. A compound represented by General Formula (1), $$P^1-L^1-(A^1-Z^1)_{m1}-A^2-\!=\!=\!-A^3-Y-A^4-(Z^2-A^5)_{m2}-L^2-P^2 \quad \text{General Formula (1)}$$

in General Formula (1),

P$^1$ represents a polymerizable group represented by any one of the following General Formulae (P-1) to (P-3), (P-7) to (P-13) and (P-15) to (P-19), P$^2$ represents a hydrogen atom or a substituent, L$^1$ and L$^2$ each independently represent a single bond or a divalent linking group, A$^1$ to A$^5$ each independently represent an aromatic hydrocarbon ring group or aromatic heterocyclic group which may have a substituent, Z$^1$ and Z$^2$ each independently represent a single bond or a divalent linking group, Y represents —CO—NH— or —NH—CO—, and m1 and m2 each independently represent an integer of 0 to 2, and m1+m2 represents an integer of 0 to 2, (P-1)

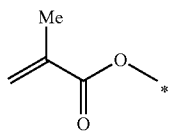 (P-2)

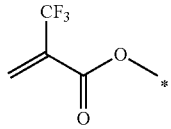 (P-3)

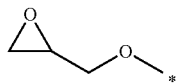 (P-7)

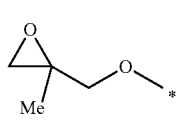 (P-8)

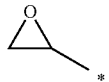 (P-9)

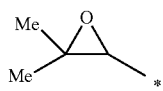 (P-10)

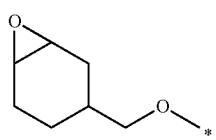 (P-11)

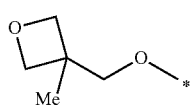 (P-12)

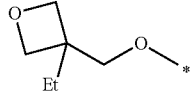 (P-13)

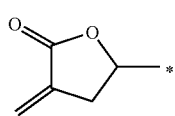 (P-15)

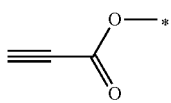 (P-16)

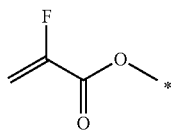 (P-17)

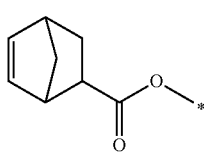 (P-18)

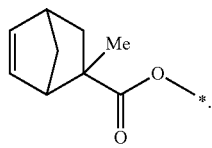 (P-19)

2. The compound according to claim 1,
wherein at least one of $A^2$, $A^3$, or $A^4$ is an aromatic hydrocarbon ring group having a substituent, or an aromatic heterocyclic group having a substituent.

3. The compound according to claim 2,
wherein the substituent of the aromatic hydrocarbon ring group is a fluorine atom, a chlorine atom, a fluoroalkyl group, an alkoxy group, or an alkyl group, or
the substituent of the aromatic heterocyclic group is a fluorine atom, a chlorine atom, a fluoroalkyl group, an alkoxy group, or an alkyl group.

4. The compound according to claim 2,
wherein the substituent of the aromatic hydrocarbon ring group is a fluoroalkyl group, an alkoxy group, or an alkyl group, or
the substituent of the aromatic heterocyclic group is a fluoroalkyl group, an alkoxy group, or an alkyl group.

5. The compound according to claim 1,
wherein $Z^1$ and $Z^2$ are each independently a single bond, —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, or —C≡C—.

6. The compound according to claim 1,
wherein $Z^1$ and $Z^2$ are each independently a single bond, —COO—, —OCO—, —CO—NH—, —NH—CO—, or —C≡C—.

7. The compound according to claim 1,
wherein L' is a group represented by General Formula (2), and $L^2$ is a group represented by General Formula (3), $$*1\!-\!\!\left(\!S^1\!-\!X^1\!\right)_{\!n1}\!\!-\!*2 \qquad \text{General Formula (2)}$$

$$*3\!-\!\!\left(\!X^2\!-\!S^2\!\right)_{\!n2}\!\!-\!*4 \qquad \text{General Formula (3)}$$

in General Formulae (2) and (3),
$S^1$ and $S^2$ each independently represent an alkylene group which may contain a heteroatom,
$X^1$ and $X^2$ each independently represent a single bond, —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH₂CH₂—OCO—, —COO—CH₂—, —OCO—CH₂—, —CH₂—COO—, —CH₂—OCO—, —CH=CH—, —N=N—, —CH=N—N=CH—, —CF=CF—, or —C≡C—, and n1 and n2 each independently represent an integer of 0 to 8, in General Formula (2),

*1 represents a bonding position with P¹ in General Formula (1), and *2 represents a bonding position with A¹ in General Formula (1), in General Formula (3),

*3 represents a bonding position with A⁵ in General Formula (1), and *4 represents a bonding position with P² in General Formula (1).

8. The compound according to claim 7, wherein X¹ and X² are each independently a single bond, —O—, —COO—, or —OCO—.

9. The compound according to claim 7, wherein n1 and n2 are each 1.

10. The compound according to claim 1, wherein m1+m2 is 0 or 1.

11. A composition comprising:
the compound according to claim 1.

12. The composition according to claim 11, further comprising a polymerization initiator.

13. The composition according to claim 11, further comprising a chiral agent.

14. A cured object, obtained by curing the composition according to claim 11.

15. An optically anisotropic body, obtained by curing the composition according to claim 11.

16. A reflective film, obtained by curing the composition according to claim 11.

17. The compound according to claim 3,
wherein the substituent of the aromatic hydrocarbon ring group is a fluoroalkyl group, an alkoxy group, or an alkyl group, or
the substituent of the aromatic heterocyclic group is a fluoroalkyl group, an alkoxy group, or an alkyl group.

18. The compound according to claim 2,
wherein Z¹ and Z² are each independently a single bond, —O—, —S—, —OCH₂—, —CH₂O—, —CH₂CH₂—, —CO—, —COO—, —OCO—, —CO—S—, —S—CO—, —O—CO—O—, —CO—NH—, —NH—CO—, —SCH₂—, —CH₂S—, —CF₂O—, —OCF₂—, —CF₂S—, —SCF₂—, —CH=CH—COO—, —CH=CH—OCO—, —COO—CH=CH—, —OCO—CH=CH—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, —CH₂—OCO—, —CH=CH—, —N=N—, —CH=N—N=CH—, —CF=CF—, or —C≡C—.

19. The compound according to claim 3,
wherein Z¹ and Z² are each independently a single bond, —O—, —S—, —OCH₂—, —CH₂O—, —CH₂CH₂—, —CO—, —COO—, —OCO—, —CO—S—, —S—CO—, —O—CO—O—, —CO—NH—, —NH—CO—, —SCH₂—, —CH₂S—, —CF₂O—, —OCF₂—, —CF₂S—, —SCF₂—, —CH=CH—COO—, —CH=CH—OCO—, —COO—CH=CH—, —OCO—CH=CH—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, —CH₂—OCO—, —CH=CH—, —N=N—, —CH=N—N=CH—, —CF=CF—, or —C≡C—.

20. The compound according to claim 4,
wherein Z¹ and Z² are each independently a single bond, —O—, —S—, —OCH₂—, —CH₂O—, —CH₂CH₂—, —CO—, —COO—, —OCO—, —CO—S—, —S—CO—, —O—CO—O—, —CO—NH—, —NH—CO—, —SCH₂—, —CH₂S—, —CF₂O—, —OCF₂—, —CF₂S—, —SCF₂—, —CH=CH—COO—, —CH=CH—OCO—, —COO—CH=CH—, —OCO—CH=CH—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, —CH₂—OCO—, —CH=CH—, —N=N—, —CH=N—N=CH—, —CF=CF—, or —C≡C—.

* * * * *